United States Patent [19]

Mezaache et al.

[11] Patent Number: 6,165,512
[45] Date of Patent: *Dec. 26, 2000

[54] DOSAGE FORMS CONTAINING TASTE MASKED ACTIVE AGENTS

[75] Inventors: Djelila Mezaache, Laurel, Md.; Michael G. Raiden, Corona, Calif.; Pradeepkumar P. Sanghvi, Herndon; Scott J. Szedlock, Sterling, both of Va.

[73] Assignee: Fuisz Technologies Ltd., Chantilly, Va.

[*] Notice: This patent is subject to a terminal disclaimer.

[21] Appl. No.: 09/183,501

[22] Filed: Oct. 30, 1998

[51] Int. Cl.$^7$ ...................................................... A61K 9/14
[52] U.S. Cl. .......................... 424/489; 424/464; 424/469; 424/490; 424/494; 424/495; 424/502
[58] Field of Search ..................................... 424/464, 469, 424/489, 490, 494, 495, 502

[56] References Cited

U.S. PATENT DOCUMENTS

| | | | |
|---|---|---|---|
| 5,387,431 | 2/1995 | Fuisz | 426/658 |
| 5,429,836 | 7/1995 | Fuisz | 426/601 |
| 5,458,823 | 10/1995 | Perkins et al. | 264/8 |
| 5,501,858 | 3/1996 | Fuisz | 424/439 |
| 5,587,172 | 12/1996 | Cherukuri et al. | 424/401 |
| 5,601,076 | 2/1997 | Battist et al. | 127/58 |
| 5,683,720 | 11/1997 | Myers et al. | 424/489 |
| 5,834,033 | 11/1998 | Abdi et al. | 425/8 |
| 5,851,454 | 12/1998 | Rutkowski et al. | 264/8 |
| 5,869,098 | 2/1999 | Misra et al. | 424/484 |

FOREIGN PATENT DOCUMENTS

| | | | |
|---|---|---|---|
| 0 353 045 A2 | 1/1990 | European Pat. Off. | A61K 37/36 |
| 0 559 897 A1 | 9/1993 | European Pat. Off. | A61K 9/50 |
| WO 95/34290 | 12/1995 | WIPO | A61K 9/14 |
| WO 95/34293 | 12/1995 | WIPO | A61K 9/20 |

*Primary Examiner*—Gollamudi S. Kishore
*Assistant Examiner*—Lakshmi Channavajjala
*Attorney, Agent, or Firm*—John F. Levis; Richard D. Schmidt

[57] ABSTRACT

The invention relates to compositions useful for making taste-masked oral dosage forms which can be easily processed and which disintegrate rapidly when placed in the mouth. The compositions include coated liquiflash particles and shearform floss particles. Tablets are preferred dosage forms.

10 Claims, No Drawings

DOSAGE FORMS CONTAINING TASTE MASKED ACTIVE AGENTS

RELATED APPLICATIONS

This invention is related to U.S. patent application Ser. No. 09/132,986 filed Aug. 12, 1998 now U.S. Pat. No. 6,048,541; U.S. Provisional Patent Application Ser. No. 60/056,617, filed Aug. 20, 1997; and U.S. patent application Ser. No. 08/914,972, also filed Aug. 20, 1997. Their disclosures are incorporated herein by reference.

FIELD OF THE INVENTION

The invention deals with dosage forms, such as tablets and lozenges, which, when ingested, quickly dissolve in the mouth, but which effectively mask the taste of unpleasant active agent(s) therein.

Also, it deals with readily processable compositions having enhanced cohesive and self-binding properties which permit shaping, e.g., tableting, without added binding agents.

BACKGROUND OF THE INVENTION

The production of microspheres containing active agent(s) is described in co-owned U.S. Pat. No. 5,683,720, incorporated herein by reference. The patent deals with the use of liquiflash processing to spheronize compositions containing one or more active agents. Acetaminophen is mentioned in Examples II and III of the patent.

EPO publication 0559 897 discloses quick release dosage forms made by coating drugs with a mixture of carnauba wax and Pluronics. The coating is said to taste mask the drug and enhance its release.

EPO publication 0353045 shows subcutaneous implants based on pellets containing somatropin, Pluronic surfactant and carnauba wax. See Example 3 therein.

In the past, the processability of tabletable compositions was enhanced by using glycerine, as a binding agent, to lend stickiness to the formulations. Some stickiness is desirable, serving to provide cohesion to hold the ingredients together during shaping and/or compression. However, in certain situations, glycerine can produce too much stickiness, resulting in the formulations' clumping or sticking in various machine parts before and during shaping and compression.

The excessive stickiness caused by the use of binders, e.g., glycerine, is overcome by employing self-binding compositions. Self-binding, readily flowable compositions containing no glycerine are described in U.S. Ser. No. 08/915,068, filed Aug. 20, 1997, now U.S. Pat. No. 5,840,331 and U.S. Ser. No. 08/914,972, also filed Aug. 20, 1997.

One way to provide self-binding flowable formulations is to formulate using shearform matrices or flosses. These matrices result when using certain processing techniques, such as the following:

U.S. Pat. No. 5,587,172, incorporated herein by reference, discusses the use of flash heat techniques to produce sucrose-containing shearform flosses, which are then processed to yield quick-dissolving tablets.

The use of shearform matrices for forming comestible units is described in WO95/34290 (published Dec. 21, 1995) from co-assigned PCT application No. PCT/US95/07144, filed Jun. 6, 1995. This case discloses a quick dissolving tablet which is formed by: (1) using flash-flow technology to provide a shearform matrix; (2) combining the partially recrystallized shearform matrix with an additive to form flowable, compactible particulate blends; and (3) compacting the blends at relatively low pressures to produce dosage forms, such as tablets.

Additionally, PCT publication WO 95/34293 (published Dec. 21, 1995) from co-assigned PCT Application No. PCT/US95/07194, filed Jun. 6, 1995, discloses a process and apparatus for making rapidly dissolving dosage forms by flash-flow processing. In this PCT application, a shearform matrix is formed by the flash-flow process, the shearform matrix is combined with an additive, and the matrix is molded to make a unit dosage form.

While shearform matrices are an advance in the art, there still exists a need for non-sticking tabletable compositions which, can be used to make fast-dissolving, pleasant tasting dosage forms. This invention addresses that need.

SUMMARY OF THE INVENTION

The invention provides compositions and shaped oral dosage forms made therefrom having improved properties. Among those properties are improved processability before shaping and enhanced dissolution and taste-masking properties when the dosage forms are used.

Co-owned U.S. patent applications Ser. No. 08/915,068, filed Aug. 20, 1997, now U.S. Pat. No. 5,840,331; and Ser. No. 09/132,986, filed Aug. 12, 1998, now U.S. Pat. No. 6,048,541, describe tablet formulations derived from saccharide-based carriers in which the use of a unique combination of feedstock ingredients yields self-binding, flowable matrices and tablet compositions. This combination—which uses a blend of sugar alcohols, i.e., sorbitol and xylitol—is superior to glycerine in providing cohesive properties and flowability.

Shapeable, preferably tabletable, compositions derived from partially hygroscopic matrices containing these sugar alcohols are useful—in the presence of tableting aids and crystallization promoters—in both high—and low-pressure tableting processes. Tablets and other dosage forms, e.g., lozenges, made therefrom rapidly dissolve when placed in the mouth, generally in less than 30 seconds.

The compositions of the invention are based on matrices, or flosses, which comprise at least one sugar alcohol, which matrices are generally considered "single floss" or "unifloss" systems. These systems are exemplified by xylitol-containing shearform matrixes, or flosses, containing a carrier and two or more sugar alcohols.

Various ingredients, such as coated microspheres containing active agent(s), are added, in suitable amounts, to the compositions of the present invention after the matrices are collected and chopped, but before they are shaped, e.g., by tabletting.

Highly useful dosage forms result when microspheres made from compositions containing active agents, solubilizers and spheronization aids are coated with taste-masking agents, then combined with flosses and conventional pharmaceutical ingredients. The resultant tablets enjoy the processing ease associated with the use of glycerine-free flosses and the taste and release properties associated with coated microspheres.

DETAILED DESCRIPTION OF THE INVENTION

Unless otherwise stated, the parts and percentages used in the specification are weight percentages, based upon total composition weight. All disclosures referred to herein are hereby incorporated by reference.

The invention relates to shapable compositions to be used to make oral dosage forms and to processes for making dosage forms using same.

Generally, Applicants' compositions contain:

(a) coated liquiflash particles containing about 80.0 to about 90.0% acetaminophen, about 5.0 to about 10.0% carnauba wax, and about 2.5 to about 10.0% Pluronic F68; and (b) glycerine-free bodies containing about 75.0 to 85.0% sucrose, about 8.0 to about 15.0% sorbitol, and about 5.0 to about 15.0% xylitol.

Also, a process is disclosed for preparing fast dissolving dosage forms. That process comprises the steps:

(1) providing liquiflash particles containing active agent (s), solubilizer(s) and spheronization aid(s), (2) coating the particles of step (1) with a cellulosic taste-masking material, (3) blending the coated particles of step (2) with glycerine-free bodies, and (4) shaping the blend to produce dosage forms.

Applicants have found that by using a combination of coated liquiflash particles and glycerine-free bodies made using specific techniques and containing certain ingredients, dosage forms that dissolve quickly in the mouth, with optional chewing, can be produced using conventional tableting equipment.

In addition, even though pressures of about 500 psi to about 10,000 psi or higher can be used on the inventive compositions, the dissolution time, in the mouth, for tablets made from this composition is in the range of from about 3 seconds to about 30 seconds. Prior art compositions required the use of specialized, low-pressure (less than 1000 psi) tableting equipment.

Additionally, it is now possible to prepare an at least partially crystalline tabletable composition, containing an active agent, with sufficient "flow" characteristics and properties to enable one to transport the composition to and through conventional tableting equipment using gravity, forced air or vacuum. This composition can then be compacted under a wide range of tableting conditions.

The terms "matrix", "floss" and "glycerine-free bodies" are used interchangeably herein.

The preparation of flosses suitable for use in the present invention is disclosed in co-assigned patent publications WO 95/34290 and WO 95/34293, both incorporated herein by reference. Preferably, the floss is a "shearform matrix" produced by subjecting a feedstock which contains a sugar carrier to flash-heat processing.

In the flash-heat process, the feedstock is simultaneously subjected to centrifugal force and to a temperature gradient which raises the temperature of the mass to create an internal flow condition which permits part of it to move with respect to the rest of the mass. The flowing mass exits through openings provided in the perimeter of a spinning head. The temperature gradient is supplied using heaters or other means which cause the mass' temperature to rise. Centrifugal force in the spinning head flings the internally flowing mass outwardly, so that it reforms as discrete fibers with changed structures.

One apparatus which produces suitable conditions is a modified floss making machine, such as that described in U.S. Pat. No. 5,854,344.

Spinning is typically conducted at temperatures and speeds of about 150° C. to 250° C. and 3,000 to 5,000 rpm, respectively. Suitable spinner heads include that disclosed in U.S. Pat. No. 5,458,823, assigned to Applicants' assignee.

Other apparatuses and processes which provide similar forces and temperature gradient conditions can be used.

The matrices used herein include, as feedstock ingredients, carrier materials, which carriers comprise at least one ingredient selected from materials which are capable of undergoing the physical and/or chemical changes associated with flash heat processing. Useful carriers include carbohydrates which become free-form particulates when flash heat processed. Saccharide-based carriers, including saccharides (i.e., sugars), polysaccharides and mixtures thereof can be also used.

The feedstocks used in the invention can include carriers chosen from various classes of "sugars." "Sugars" are those substances which are based on simple crystalline mono- and di-saccharide structures, i.e., based on $C_5$ and $C_6$ sugar structures. They may include glucose, sucrose, fructose, lactose, maltose, pentose, arbinose, xylose, ribose, mannose, galactose, sorbose, dextrose and sugar alcohols, such as sorbitol, mannitol, xylitol, maltitol, isomalt, sucralose and the like and mixtures thereof. Sucrose is the preferred sugar.

Useful mixtures of carriers include the sugars listed above along with additional mono- di-, tri- and polysaccharides. Additional saccharides can be used in amounts of up to 50% by weight, preferably up to 30%, most preferably up to 20%, of the total carbohydrate content.

Optionally, the polysaccharides can be used alone as carriers. Polysaccharide carriers include polydextrose and the like. Polydextrose is a non-sucrose, essentially non-nutritive, carbohydrate substitute. It can be prepared through polymerization of glucose in the presence of polycarboxylic acid catalysts and polyols. Generally, polydextrose is commercially available in three forms: polydextrose A and polydextrose K, which are powdered solids; and polydextrose N supplied as a 70% solution. U.S. Pat. No. 5,501,858 discusses polydextrose carriers.

If other carrier materials are used, they are employed in combination with sugar and not as total replacement therefor. For example, maltodextrins may be employed. Maltodextrins include mixtures of carbohydrates resulting from the hydrolysis of a saccharide. They are solids having a dextrose equivalent (DE) values up to and including about 65.

The carrier can also include maltooligo-saccharides produced by selective hydrolysis of corn starch. A general description of maltooligo-saccharides useful herein is set forth in co-owned U.S. Pat. Nos. 5,347,431 and 5,429,836.

Applicants typically use matrices which are devoid of glycerine.

In preferred embodiments, xylitol is added to a mixture of saccharide-based carrier and one or more additional sugar alcohols, with sorbitol being favored as an added sugar alcohol. The carrier mix is flash-heat processed to provide a shearform floss having self-binding properties. Flosses made using sucrose, sorbitol and xylitol have been found to yield particularly effective self-binding properties. They exemplify "single floss" or "unifloss" systems.

The ingredients which increase cohesiveness and lend self-binding properties to the glycerine-free compositions preferably include sugar alcohols, such as sorbitol, xylitol, maltitol, mannitol and mixtures thereof, all of which form flosses. It is believed that the hygroscopic nature of these sugar alcohols increases the cohesiveness and self-binding character of matrices and matrix-containing formulations. Other sugar alcohols, especially hygroscopic ones, are contemplated.

Xylitol and sorbitol are the preferred sugar alcohols. Effective amounts of xylitol in the flosses are between about 0.5% and 25%, and preferably about 10% by weight. Sorbitol is used in the flosses in amounts of about 0.5% to about 40%.

When sorbitol and xylitol are used, the ratio of sorbitol to xylitol is from about 1:0.1 to about 1:10.

The total floss content preferably includes about 50 to about 85% sucrose, about 5 to about 20% sorbitol and about 5% to about 25% xylitol.

In some cases, flosses are used along with bio-affecting, or active, agents in the form of microsphere granulates or crystalline particles in the shaping/compressing process. It is preferred that the bio-affecting agents be coated. A xylitol-containing floss can be added to microspheres of one or more active agents. Typically, the weight ratio of total floss to microspheres is about 1:1. In these instances, about 5% to about 25% of the floss is xylitol.

The amorphous shearform matrix of the present invention is preferably made from a feedstock which includes sucrose, sorbitol, xylitol and Tween 80. As set forth in U.S. Ser. No. 08/915,068, filed Aug. 20, 1997, these compositions have superior cohesiveness. In addition, the matrices, when partially recrystallized, yield matrix-containing mixes having particulate flowability such that they are suitable for use in high-speed and high-pressure tableting equipment to yield fast-dissolving tablets.

Compositions to be processed into dosage forms generally contain one or more conventional food/pharmaceutical additives. Conventional quantities of same may be incorporated into one or more of the matrices or may be mixed therewith prior to tableting or other shaping. Useful amounts of conventional additives range from about 0.01% to about 80% by weight, based on the weight of the matrices or formulations in which they are used. The quantities may vary from these amounts, depending on the functions of the additives and the characteristics desired in the matrices and/or the final tablet compositions.

Conventional tableting aids and additives may be selected from a wide variety of materials such as lubricants, glidants, anti-caking agents and flow agents. For example, lubricants such as magnesium stearate, calcium stearate, sodium chloride, zinc stearate, hydrogenated vegetable oils, sterotex, polyoxyethylene, glyceryl monostearate, talc, polyethylene glycol, sodium benzoate, sodium lauryl sulfate, magnesium lauryl sulfate, sodium stearyl fumarate, adipic acid, light mineral oil and the like may be employed, with sodium stearyl fumarate preferred. Waxy fatty acid esters, such as glyceryl behenate, sold as "Compritol" products, can be used. Mixtures are operable.

Lubricants are used in amounts ranging from about 0% to about 10%, with about 0.1% to about 5.0% typically used.

Glidants such as starch, talc, lactose, stearates, dibasic calcium phosphate, magnesium carbonate, magnesium oxide, calcium silicate, Cabosil™, Syloid™, and silicon dioxide aerogels may be employed.

Lactose, which may be a glidant or filler, can be added to the chopped floss at about 2% concentration to inhibit clumping. Generally, the floss is chopped in the presence of lactose.

Glidants are present in amounts of about 0% to about 20%, with typical amounts being about 0.1% to about 5.0%.

The preformed matrices produced in accordance herewith are generally rendered partially crystalline, either alone or in the presence of additives, by one or more of the following crystallizing techniques.

The nature of the matrix feedstock determines whether the matrix is to be crystallized or recrystallized after it is formed. Highly amorphous feedstocks are crystallized. Crystalline ones are recrystallized. Nonetheless, the terms "crystallization" and "recrystallization" are used interchangeably in the following discussion.

The amorphous matrices are typically recrystallized by incorporating into, or contacting them with one or more crystallization promoters, termed "crystallization enhancers" and "crystallization modifiers." Both types of promoters assist in the recrystallization.

One technique for recrystallizing involves the use of crystallization enhancers. These are generally forces or physical materials that are used after the floss has been formed, but before the floss-containing composition is tableted. Suitable crystallization enhancers include ethanol, polyvinylpyrrolidone, water (e.g. moisture), glycerine, radiant energy (e.g., microwaves, heat, etc.) and the like. Combinations can be used. When recrystallization involves physical materials, as enhancers, typical amounts of these enhancers range from about 0.01% to about 10.0% by weight of the tablet composition.

Another crystallization technique involves crystallization modifiers. These crystallization modifiers are either (a) floss ingredients used at levels of about 0.01% to about 20.0% by weight of the floss, or (b) a combination of ingredients (a) with environmental agents or forces such as increased moisture and heat. The combination of additives with heat/humidity is called "aging."

Surfactants are preferred crystallization modifiers. Other materials which are non-saccharide hydrophilic organic materials may also be used. Useful modifiers preferably have a hydrophilic to lipid balance (HLB) of about 6 or more. Such materials include, without limitation, anionic, cationic, and zwitterionic surfactants as well as neutral materials with suitable HLB values. Hydrophilic materials having polyethylene oxide linkages are effective. Those with molecular weights of at least about 200, preferably at least 400, are highly useful.

Crystallization modifiers useful herein include: lecithin, polyethylene glycol (PEG), propylene glycol (PPG), dextrose, the SPANS and TWEENS which are commercially available from ICI America, and the surface active agents known as "Carbowaxes". Generally, the polyoxyethylene sorbitan fatty acid esters called TWEENS, or combinations of such modifiers are used. Crystallization modifiers are usually incorporated into matrices in amounts of between about 0% and 10%.

Whether they are physical materials or forces, crystallization modifiers and/or enhancers are used at levels sufficient to give the floss/additive mixes the cohesivity and particular flowability needed for further processing, e.g., molding into tablets.

The matrices are allowed to recrystallize, with or without added crystallization assistants, i.e., modifiers and enhancers, either before or after they are combined with the non-matrix component(s), e.g., microspheres or other liqui-flash particles containing bio-affecting additives(s). The recrystallization level of the matrix generally reaches at least about 10% before tableting. Crystallization levels of 20% or more are highly effective. The use of partially recrystallized matrices leads to compositions that are free flowing and tabletable using conventional machines. U.S. Pat. No. 5,597,416 describes a process for recrystallizing in the presence of additives.

Methods for effecting the recrystallization of the matrices include one or more of the following: use of Tween 80 or other crystallization modifier(s) in the matrix premix; aging of the matrix for up to several weeks; contacting the matrix with sufficient moisture and heat to induce crystallization;

and treating the floss or the floss-containing composition with ethanol, ethanol vapors or another crystallization enhancer. Combinations of these may be used so that the matrices may be contacted with a crystallization enhancer while they are also in contact with moisture or heat.

When a surfactant, such as a Tween, is used, about 0.001% to about 1.00% is included in the floss preblend as a crystallization modifier. Following preblending, the formulations are processed into flosses, then chopped and used, with or without additives, to make tablets. Mixtures of surfactants can be used.

When ethanol is used as a crystallization enhancer it is used in amounts, based upon the weight of the matrix, of about 0.1% to about 10%, with amounts of about 0.5% to about 8.0% being very effective. The preformed matrix is contacted with ethanol. Excess ethanol is evaporated by drying for about an hour at about 85° F. to about 100° F., with 95° F. being highly useful. The drying step is carried out using tray drying, a jacketed mixer or other suitable method. Ethanol vapors may also be used. Following ethanol treatment, the matrix becomes partially recrystallized on standing for a period ranging from about a few hours up to several weeks. When the floss is about 5% to about 30% recrystallized, it is chopped/milled and tableted after blending with other ingredients. The tableting compositions flow readily and are cohesive.

When chewable products are made, it is preferred that partially crystalline ethanol-treated flosses be used. Such flosses are generally chopped in the presence of lactose before ethanol treatment.

U.S. Pat. No. 5,601,076, assigned to Applicants' assignee and incorporated herein by reference, discloses the use of ethanol to promote crystallization of surfactant-containing flosses.

Recrystallization of the matrix may take place in the presence suitable quantities of one or more bio-affecting agents and/or other additives.

The matrix portions of the compositions are typically formed via flash-heat processing into a floss. The strands of the floss are macerated or chopped into rods for further processing. The rods of chopped floss have lengths of about 50 to about 500 microns.

When active agents, such as bio-affecting agents, are added, they are often added in the form of particles, and generally as uniform microspheres. Suitable microspheres and other spheroidal particles can be made by "liquiflash" processes. The microspheres may be coated.

"Liquiflash" processing involves the use of heat and pressure to reduce the feedstock to a condition in which resistance to flow, e.g., viscosity, which impedes the propensity to form liquid droplets, is eliminated. In this condition, the mass has become liquid or "liquiform." Once all resistance to flow is gone, shear force is applied to the feedstock until discrete particles separate from the mass. The particles, called "shearlite" particles, have a size and shape influenced only by natural mass separation of the flowing feedstock. U.S. Pat. Nos. 5,458,823 and 5,683,720, both incorporated herein by reference, describe such processing.

The inventive compositions include liquiflash particles, which are generally spherical in shape. Useful particles are usually microspheres having mean diameters of about 100 to about 200 microns, with mean diameters of about 150 to about 200 microns being preferred and those of about 160 to about 170 microns being highly preferred.

When coated, the particles have mean diameters of about 175 to about 250 microns, with those of about 200 microns being preferred. Coating levels of about 10% to about 40%, with levels of about 30% preferred, are used to apply coatings.

Coatings can applied for a variety of reasons. Generally, taste-masking and/or controlled release coatings are used. Taste-masking coatings are the preferred type of coatings applied.

Coatings are applied using conventional devices, such as fluidized bed coating machines.

The liquiflash particles used herein contain one or more active ingredients, such as bio-affecting agents. These are typically prescription or over the counter medications.

The active ingredients useful herein can be selected from a large group of therapeutic agents. Respective classes include those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; anti-tumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents which may be used in the invention include: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorhydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diprorionate; benzocaine; benzoic acid; benzophenones; benzoyl peroxide; benzquinamide and its hydrochloride; bethanechol; biotin; bisacodyl; bismuth subsalicylate; bornyl acetate; brompheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine and its hydrochloride; cinnamedrine hydrochloride; citalopram; citric acid; clarithromycin; clemastine and its fumarate; clonidine and its hydrochloride salt; clorfibrate; cocoa butter; cod liver oil; codeine and its fumarate and phosphate; cortisone acetate; ciprofloxacin HCl; cyanocobalamin; cyclizine hydrochloride; cyproheptadine and its hydrochloride; danthron; dexbrompheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fluoxetine; folic acid; fosphenytoin; 5-fluorouracil (5-FU); fluoxetine and its hydrochloride; flurbiprofen; furosemide; gabapentan; gentamicin; gemfibrozil; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; meclizine and its hydrochloride; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole and its hydrochloride; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

Particularly useful active agents are sparingly soluble solid agents whose dissolution and release properties are enhanced by the solubilizing agents used herein. These agents include $H_2$ antagonists, analgesics, including non-steroidal anti-inflammatory drugs (NSAIDs), anticholesterolemics, anti-allergy agents, and anti-migraine agents.

Analgesics include aspirin, acetaminophen, acetaminophen plus caffeine, and non-steroidal anti-inflammatory drugs (NSAIDS), e.g., ibuprofen and nimesulide.

Useful NSAIDs include ibuprofen; diclofenac and its alkali metal salts; fenoprofen and its metal salts; flurbiprofen; ketoprofen; naproxen and its alkali metal salts; nimesulide; and piroxicam and its salts.

$H_2$-antagonists which are contemplated for use in the present invention include cimetidine, ranitidine hydrochloride, famotidine, nizatidine, ebrotidine, mifentidine, roxatidine, pisatidine and aceroxatidine.

Useful anti-allergy agents include hydricodone and its tartrates; clemastine and its fumarate; azatadine and its maleate; acetaminophen; hydroxyzine and its pamoate and hydrochloride salts; chlorpheniramine and its maleates and tannates; pseudoephedrine and its sulfates and hydrochlorides; bromopheniramine and its maleate; dextromethorphan and its hydrohalides; loratadine; phenylephrine and its tannates and hydrochlorides; methscopolamine and its nitrates; phenylpropanolamine and its hydrochlorides; codeine and its hydrochloride; codeine and its phosphate; terfenadine; acrivastine; astemizole; cetrizine and its hydrochloride; phenindamine and its tartrate; tripelennamine and its hydrochloride; cyproheptadine and its hydrochloride; promethazine and its hydrochloride; and pyrilamine and its hydrochlorides and tannates.

Useful antimigraine agents include divalproex and its alkali metal salts; timolol and its maleate; propanolol and its hydrohalides; ergotamine and its tartrate; caffeine; sumatriptan and its succinate; dihydroergotamine, its hydrogenates/mesylates; methsergide and its maleate; isometheptene mucate; and dichloralphenazone.

Another class of drugs which can be used are antiemetics. Useful antiemetics include: meclizine and its hydrochloride; hydroxyzine and its hydrochloride and pamoate; diphenhydramine and its hydrochloride; prochlorperazine and its maleate; benzquinamide and its hydrochloride; granisetron and its hydrochloride; dronabinol; bismuth subsalicylate; promethazine and its hydrochloride; metoclopramide and its halides/hydrates; chlorpromazine; trimethobenzamide and its hydrochloride; thiethylperazine and its maleate; scopolamine; perphenazine; and ondansetron and its hydrochloride.

Other active ingredients for use in the present invention include antidiarrheals such as immodium AD, antihistamines, antitussives, decongestants, vitamins, and breath freshners. Also contemplated for use herein are anxiolytics such as Xanax; antipsychotics such as Clozaril and Haldon; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigranes such as Imigran, ACE-inhibitors such as Vasotec, Capoten and Zestril; Anti-Alzheimers agents such as Nicergoline; and $Ca^{II}$-Antagonists such as Procardia, Adalat, and Calan.

Among the anticholesterolemics, the statins, e.g., lovastatin, provastatin and the like are notable.

Combinations of various types of drugs, as well as combinations of individual drugs, are contemplated.

The spheroidal liquiflash particles used in the invention generally contain at least one active agent, at least one solubilizer and at least one spheronization aid.

Solubilizers are surfactants and other materials included in the microspheres to assist in the dissolution of the drug from the liquiflash particles. Polymeric surfactant materials containing one or more polyoxyalkylene blocks, such as poloxamers are typical. Useful solublilizers include Poloxamer 188 (also called "Pluronic F68", from BASF Corp.) and other polyoxyethylene/polyoxypropylene copolymers. Pluronic F68 is preferred. Mixtures can be used.

Spheronization aids are materials which help the drug-containing mix to form robust, durable spherical particles under liquiflash conditions. These spheronization aids include waxes and wax-like materials. Carnauba wax is preferred. When used, the carnauba wax acts as a binder, thus reducing the friability of the microspheres during handling and cooling. Mixtures are operable.

It is preferred that the liquiflash microspheres contain only active agent(s), solubilizer(s) and spheronization aid(s) and that they be coated after spheronization.

It is also preferred that the coating used on the microspheres be one or more cellulosic coatings which serve to mask the taste of any unpleasant tasting active, or bio-affecting agent(s) in the microspheres. Useful cellulosic coatings include one or more alkylcellulose and/or hydroxyalkylcellulose polymers. Ethyl cellulose(EC)/-hydroxypropylcellulose (HPC) blends are useful, with EC:HPC ratios of 0.1:1 to 2:1 being useful. One preferred combination is a 1:1 blend of these polymers.

The cellulosic coatings are generally applied to the liquiflash particles after spheronization from organic solvent solution. Typical solvents include one or more of acetone, alkyl alcohols (e.g., isopropyl alcohol), and the like.

Fluidized bed coating machines, e.g., the Glatt GPCG-60, and the like can be used.

The coatings applied to the liquiflash particles may contain ingredients other than the cellulosics. Thus, one or more colorants, flavorants, sweeteners, controlled release agents and the like can also be used in the coating formulations.

Other ingredients which may be mixed with the floss particles and coated liquiflash particles are fillers, fragrances, dyes, flavors, glidants, flow control agents, thickeners, sweeteners (both artificial and natural), and other conventional tablet additives. These ingredients are generally used in amounts of about 0.001% to about 20%, based upon total composition weight.

For example, fillers may be used to increase the bulk of the tablet. Some of the commonly used fillers are silicon dioxide (silica), calcium sulfate, both di- and tri-basic; starch; calcium carbonate; microcrystalline cellulose; modified starches, lactose, sucrose; mannitol and sorbitol.

Flavors may be chosen from natural and synthetic flavoring liquids. An illustrative list of such agents includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such a lemon, orange, grape, lime and grapefruit, and fruit essences, including apple, pear, peach, grape, strawberry, raspberry, cherry, plum, pineapple, apricot, or other fruit flavors. Grape flavoring is among the preferred flavors.

Other useful flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); mixtures thereof and the like.

The sweeteners may be chosen from the following non-limiting list: glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; *Stevia Rebaudiana* (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof. Acesulfame potassium is a preferred sweetener. Other sweeteners may be used, alone or in mixtures.

Other ingredients include binders, other than glycerine, which contribute to the ease of formation and general quality of the tablet. Binders include starches, pregelatinized starches, gelatin, polyvinylpyrrolidone, methylcellose, sodium carboxymethylcellulose, ethylcellulose, polyacrylamides, polyvinyloxoazolidone and polyvinylalcohols.

Color additives can be used in preparing tablets. Such color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Using the invention, strong, highly attractive dosage forms, e.g., tablets or lozenges, can be produced having textures and internal structures which are relatively open to solubilization. Applicants' compositions are preferably formed into tablets at pressures of from about 500 up to about 6,000 psi. using conventional tabletting machines, such as a rotary tablet press.

When chewable dosage forms are made, they are typically compressed to hardnesses of about 3 to about 15 SCU's, preferably about 4 to about 6. Tablet thicknesses for chewables are about 0.2 to about 0.3 inches.

The following non-limiting examples illustrate the invention.

EXAMPLE I

Coated Acetaminophen Microspheres

Acetaminophen (APAP) powder (melting point 169–170.5° C.) was used in the following formulation to produce microspheres:

| | |
|---|---|
| APAP | 85% |
| Carnauba wax | 7.5% |
| Pluronic F68 | 7.5% |

The Pluronic was milled through a Fitzmill using a 40 mesh screen. All of the ingredients were blended in a Littleford FKM600 mixer at 60 Hz plow speed, with chopper, for 10 minutes. The blend was then subjected to liquiflash processing at 60 Hz and 37% nominal power using the 5" V-groove heater head disclosed in U.S. Ser. No. 08/874,215, filed Jun. 13, 1997. The collected microspheres were sieved. The fraction passing through a 40 mesh and retained on 120 mesh sieve was coated.

The microspheres selected were coated in a fluid bed coater for taste-masking at a 30% coating level with a coating solution containing a 1:1 ethylcellulose/hydroxypropylcellulose blend in acetone:isopropyl alcohol solvent.

EXAMPLE II

Unifloss

A preblend of 78.25% sucrose, 11.0% sorbitol, 10.0% xylitol and 0.75% TWEEN (Polysorbate) 80 was prepared.

The floss preblend was processed using the 5" crown head disclosed in U.S. Pat. No. 5,854,344, at a temperature of 250° C. and rotational speed of 60 Hz (3600 rpm). The floss collected was chopped in the Littleford FKM600 mixer with 2% lactose (2% w/w of the floss) for 2 minutes at 100 rpm with the choppers on. 200 proof ethanol (0.5% based on weight of the floss) was sprayed on the chopped floss and mixed. The floss was then dried at 45° C. for 90 minutes with intermittent mixing. The dried floss was screened through a 20 mesh screen.

EXAMPLE III

Flash Dose Tablets

The microspheres (Example I) and the floss (Example II) were used in the following composition:

| Component | Percentage |
|---|---|
| APAP taste-masked microspheres | 47.97 |
| Floss | 48.88 |
| Grape flavor | 0.70 |
| Citric acid | 1.50 |
| Acesulfame potassium | 0.20 |
| Silicon dioxide | 0.25 |
| Sodium stearyl fumarate | 0.50 |

The coated APAP microspheres were blended with the sieved floss for 5 minutes in the Littleford FKM600 mixer, followed by the addition of flavors, sweeteners, and citric acid for another 3 minutes. Thereafter silicon dioxide was added and the mix blended for another 2 minutes. The final addition, sodium stearyl fumarate, was followed by blending for an additional 2 minutes.

The blend was then tabletted on a Kilian T200 Rotary Tablet Press using flat-faced bevel edge punches (tablet weights were 255 mg for 9 mm punch tooling, equivalent to 80 mg APAP, and 510 mg for 12 mm tooling, equivalent to 160 mg APAP dose). The hardness values ranged from 0.5 lb. to 2.0 lb.

Reasonable variations, such as those which would occur to a skilled artisan, can be made herein without departing from the scope of the invention.

We claim:

1. A composition useful for making oral dosage forms comprising:

a) liquiflash particles containing at least one bioaffecting agent and a combination of at least one solubilizer and at least one spheronization aid, said liquiflash particles being coated after spheronization; and b) glycerine-free bodies formed from a composition containing sucrose, sorbitol and xylitol.

2. The composition of claim 1 wherein the liquiflash particles are coated with at least one taste-masking coating.

3. The composition of claim 2 wherein the liquiflash particles contain acetaminophen.

4. The composition of claim 3 wherein the coating contains at least one cellulosic polymer.

5. The composition of claim 4 wherein the coating contains ethylcellulose and hydroxypropylcellulose polymers.

6. An oral dosage form produced by shaping the composition of claim 5.

7. An oral dosage form produced by shaping a composition comprising:

(a) coated liquiflash particles containing about 80.0 to about 90.0% acetaminophen, about 7.0 to about 10.0% carnauba wax, and about 7.0 to about 10.0% Pluronic F68; and (b) glycerine-free bodies containing about 75.0 to 85.0% sucrose, about 8.0 to about 15.0% sorbitol, and about 5.0 to about 15.0% xylitol.

8. An oral dosage form produced by shaping a composition comprising:

(a) coated liquiflash particles containing 85% acetaminophen, 7.5% carnauba wax, and 7.5% Pluronic F68; and (b) glycerine-free bodies containing 78.25% sucrose, 11.00% sorbitol, 10.00% xylitol and 0.75% Polysorbate 80.

9. The dosage form of claim 8 containing:

47.97% coated liquiflash particles, 48.88% glycerine-free bodies, 0.70% flavor, 1.5% citric acid, 0.2% sweetener, 0.25% silicon dioxide, and 0.50% sodium stearyl fumarate.

10. A process for preparing fast dissolving dosage forms comprising the steps:

(1) providing liquiflash particles containing active agent (s), solubilizers and spheronization aid(s), (2) coating the particles of step (1) with a cellulosic taste-making material, (3) blending the coated particles of step (2) with glycerine-free bodies, and (4) shaping the blend to produce dosage forms.

* * * * *